US012672925B2

(12) United States Patent (10) Patent No.: US 12,672,925 B2
Noguchi et al. (45) Date of Patent: Jul. 7, 2026

(54) MEDICAL APPARATUS

(71) Applicant: CANON KABUSHIKI KAISHA, Tokyo (JP)

(72) Inventors: Tomio Noguchi, Shizuoka (JP); Yusuke Niikawa, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 211 days.

(21) Appl. No.: 18/774,216

(22) Filed: Jul. 16, 2024

(65) Prior Publication Data

US 2024/0366323 A1 Nov. 7, 2024

Related U.S. Application Data

(63) Continuation of application No. PCT/JP2023/003151, filed on Feb. 1, 2023.

(30) Foreign Application Priority Data

Feb. 14, 2022 (JP) ................................. 2022-020115

(51) Int. Cl.
*A61B 34/30* (2016.01)
*A61M 25/01* (2006.01)

(52) U.S. Cl.
CPC ........ *A61B 34/30* (2016.02); *A61B 2034/301* (2016.02); *A61M 25/0113* (2013.01)

(58) Field of Classification Search
CPC .... A61B 34/30; A61B 2034/301; A61B 90/50
See application file for complete search history.

(56) References Cited

U.S. PATENT DOCUMENTS

| | | | |
|---|---|---|---|
| 8,708,952 | B2 | 4/2014 | Cohen et al. |
| 8,758,327 | B2 | 6/2014 | Tsujita et al. |
| 9,707,377 | B2 | 7/2017 | Cohen et al. |
| 10,010,699 | B2 | 7/2018 | Cohen et al. |
| 2008/0310945 | A1 | 12/2008 | Tsujita et al. |
| 2011/0105954 | A1 | 5/2011 | Cohen et al. |
| 2014/0081113 | A1 | 3/2014 | Cohen et al. |
| 2014/0243851 | A1 | 8/2014 | Cohen et al. |
| 2020/0405485 | A1* | 12/2020 | Rohl ..................... A61F 2/2466 |
| 2021/0259794 | A1 | 8/2021 | Kato et al. |

FOREIGN PATENT DOCUMENTS

| | | |
|---|---|---|
| JP | 2008-307310 A | 12/2008 |
| JP | 2011-509763 A | 3/2011 |
| JP | 2021-137566 A | 9/2021 |

* cited by examiner

*Primary Examiner* — Todd J Scherbel
(74) *Attorney, Agent, or Firm* — VENABLE LLP

(57) ABSTRACT

A medical apparatus includes a bendable medical device including a bendable body and a held portion, and an insertion unit including a moving body and a driving portion. The insertion unit is tiltable. The moving body includes a recess portion configured to accommodate the held portion in a case where the bendable medical device is attached to the moving body, a locking member that is movable between a locking position and a release position, and a restriction surface facing the recess portion. In a state in which the held portion is positioned within the recess portion and the tilt angle is maximized, the restriction surface extends upward such that an upper end of the restriction surface is positioned above a lower end of the held portion, and the upper end of the restriction surface forms a lower edge of an opening of the recess portion.

9 Claims, 9 Drawing Sheets

MEDICAL APPARATUS

CROSS-REFERENCE TO RELATED APPLICATIONS

This application is a Continuation of International Patent Application No. PCT/JP2023/003151, filed Feb. 1, 2023, which claims the benefit of Japanese Patent Application No. 2022-020115, filed Feb. 14, 2022, both of which are hereby incorporated by reference herein in their entirety.

BACKGROUND OF THE INVENTION

Field of the Invention

The present invention relates to a medical apparatus.

Description of the Related Art

U.S. Patent Application Publication No. 2021/0259794 discloses a bendable medical device that is capable of bending and an insertion unit to and from which the bendable medical device can be attached and detached. According to this document, a user can switch between a use method of holding and manually inserting the bendable medical device that is detached from the insertion unit into a patient's body, and a use method of robotically controlling insertion by attaching the bendable medical device to the insertion unit.

In such a configuration in which the bendable medical device is attachable and detachable to and from the insertion unit as described in the aforementioned document, it is desired to reduce a possibility of the bendable medical device being inadvertently dropped.

SUMMARY OF THE INVENTION

The present invention provides a medical apparatus that can reduce a possibility of a bendable medical device being dropped.

According to an aspect of the invention, a medical apparatus includes a bendable medical device including a bendable body and a held portion, the bendable body being bendable and configured to be inserted in an object, and an insertion unit including a moving body to which the bendable medical device is detachably attached, and a driving portion configured to move the moving body for advancing and retracting the bendable body with respect to the object, wherein the insertion unit is tiltable so as to change a tilt angle of the bendable medical device, which is attached to the moving body, with respect to a horizontal, wherein the moving body includes a recess portion configured to accommodate the held portion in a case where the bendable medical device is attached to the moving body, a locking member that is movable between a locking position for locking the held portion within the recess portion and a release position for allowing the held portion to disengage from the recess portion, and a restriction surface facing the recess portion, and wherein, in a state in which the held portion is positioned within the recess portion and the tilt angle is maximized, the restriction surface extends upward such that an upper end of the restriction surface is positioned above a lower end of the held portion, and the upper end of the restriction surface forms a lower edge of an opening of the recess portion.

Further features of the present invention will become apparent from the following description of exemplary embodiments with reference to the attached drawings. To be noted, in the attached drawings, the same or substantially the same elements are denoted by the same numerals.

DESCRIPTION OF THE EMBODIMENTS

Hereinafter, embodiments of the present disclosure will be described with refence to drawings.

Overview of Medical Apparatus

Figure 1:
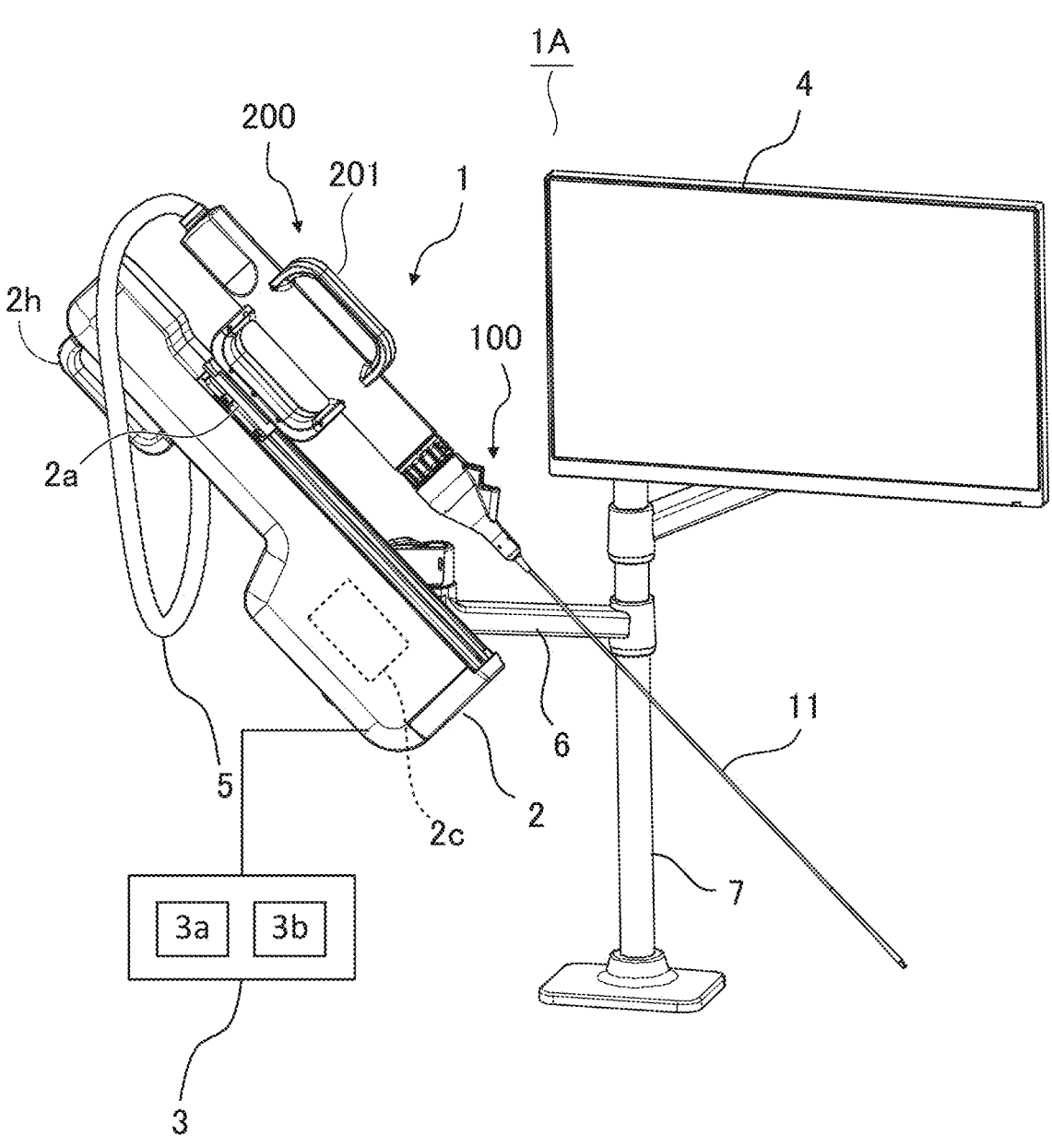
FIG. 1 is an overall view of a medical apparatus according to an embodiment.
Figure 2:
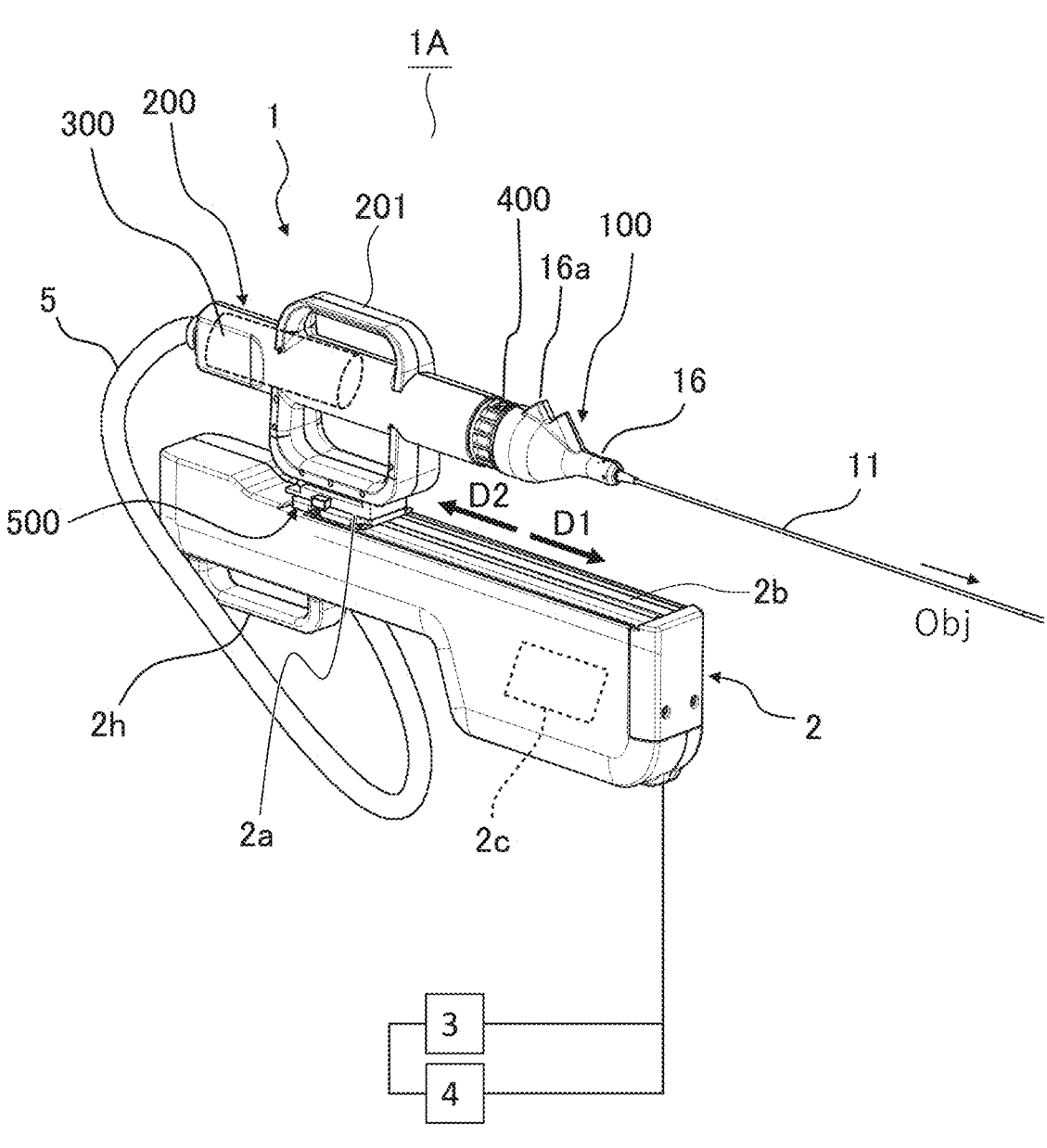
FIG. 2 is a perspective view illustrating a bendable medical device and an insertion unit.

First, using FIGS. 1 and 2, a medical apparatus 1A will be described. FIG. 1 is an overall view of the medical apparatus 1A according to an embodiment of the present disclosure. FIG. 2 is a perspective view illustrating a bendable medical device 1 and an insertion unit 2 according to the present embodiment.

As illustrated in FIG. 1, the medical apparatus 1A includes the bendable medical device 1, the insertion unit 2 to and from which the bendable medical device can be attached and detached, and a control portion 3 (controller) that controls the bendable medical device 1 and the insertion unit 2. Further, the medical apparatus 1A includes an arm 6 that supports the insertion unit 2, a monitor 4, serving as a display apparatus, and a support member 7 that supports the monitor 4 and the arm 6. To be noted, a supporting configuration of the insertion unit 2 is not limited to this, and, for example, the arm 6 may be supported by a moving base that is provided with casters so as to be movable.

The bendable medical device 1 includes a catheter unit 100 including a catheter 11 serving as a bendable body, and a base unit 200. The catheter unit 100 is configured to be attachable and detachable with respect to the base unit 200.

In the present embodiment, by inserting the catheter 11 into an object, a user of the medical apparatus 1A and the bendable medical device 1 can perform a work such as observing an inside of the object, collecting various specimens from the inside of the object, and treating the inside of the object. As one embodiment, the user can insert the catheter 11 in a patient as the object. Specifically, by insertion in a bronchial tube through the mouth or nose of the patient, a work such as observing, collecting, or cutting a lung tissue can be performed.

The catheter 11 can be used as a guide (sheath) that guides a medical tool for performing the work described above. As examples of the medical tool (medical instrument), endoscopes, forceps, and abrasion devices can be mentioned. In addition, the catheter 11 itself may have a function as the medical tools described above.

In the present embodiment, the control portion 3 includes a calculation apparatus 3*a*, and an input apparatus 3*b*. The input apparatus 3*b* receives commands and input for operating the catheter 11. The calculation apparatus 3*a* includes a storage that stores programs and various data for controlling the catheter, a random access memory, and a central processing apparatus for executing the program. In addition, the control portion 3 may include an output portion for outputting a signal for displaying an image on the monitor 4.

As illustrated in FIG. 2, the bendable medical device 1 is electrically connected to the control portion 3 via a cable 5 interconnecting the base unit 200 and the insertion unit 2. The bendable medical device 1 receives, for example, a power and a drive command for driving a wire drive unit 300, described below, via the cable 5. To be noted, the bendable medical device 1 and the control portion 3 may be directly connected to each other via a cable. The bendable medical device 1 and the control portion 3 may be wirelessly connected to each other.

The insertion unit 2 includes a moving stage 2*a*, serving as a moving body, and a slider 2*b* that is linearly movable (slidable) while supporting the moving stage 2*a*, and a motor 2*c*, serving as a driving portion (first driving portion) that drives the moving stage 2*a* (moving body). The motor 2*c* rotates based on the drive command from the control portion 3, and drives the moving stage 2*a* via a transmission mechanism, not shown.

The bendable medical device 1 is detachably attached to the insertion unit 2 via the base unit 200. More specifically, the bendable medical device 1 is detachably attached to an attachment portion 500 (connecting portion) disposed on the moving stage 2*a*. In the base unit 200, a holding portion 201 that is provided for the user to hold at the time of attaching and detaching the bendable medical device 1 with respect to the insertion unit 2 is disposed.

Even in a state in which the bendable medical device 1 is detached from the attachment portion 500 of the moving stage 2*a*, the connection between the bendable medical device 1 and the control portion 3 is maintained such that the bendable medical device 1 can be controlled by the control portion 3. In the present embodiment, even in the state in which the bendable medical device 1 is detached from the attachment portion 500 of the moving stage 2*a*, the bendable medical device 1 and the insertion unit 2 are interconnected via the cable 5. Therefore, even in a state in which the bendable medical device 1 is detached from the insertion unit 2 (at the time of manual insertion), it is possible to drivingly bend the catheter 11 by the wire drive unit 300, described below.

The bendable medical device 1 includes the wire driving portion 300 (second driving portion) for driving the catheter 11. The catheter 11 includes a bendable portion (bendable body, catheter main body) and a bending driving portion (catheter driving portion) constituted from a plurality of drive wires (linear members) configured to bend the bendable portion. In the present embodiment, the bendable portion has flexibility, and is a tubular member that includes a passage for inserting a medical device.

The bendable medical device 1 of the present embodiment is a robot catheter apparatus that drives the catheter 11 by the wire driving portion 300 controlled by the control portion 3. The control portion 3 can perform an operation of bending the catheter 11 by controlling the wire driving portion 300. More specifically, by driving each of the plurality of driving wires by a driving force of an actuator of the wire driving portion 300, the bending driving portion can bend the bendable portion toward a direction intersecting with an extending direction of the catheter 11. In the present embodiment, the wire driving portion 300 is built in the base unit 200.

Regarding the extending direction of the catheter 11, an end portion where the distal end of the catheter 11 inserted in the object is arranged will be referred to as afar end. Regarding the extending direction of the catheter 11, the opposite side of the far end will be referred to as a near end.

The catheter unit 100 includes a near end cover 16 that covers the near end side of the catheter 11. The near end cover 16 has a tool hole 16*a*. The medical tool can be inserted in the catheter 11 through the tool hole 16*a*. As described above, in the present embodiment, the catheter 11 has a function that serves as a guide apparatus for guiding the medical tool to a desired position in the inside of the object.

For example, the catheter 11 is inserted to a target position in the inside of the object with an endoscope inserted in the catheter 11. After the catheter 11 has reached the target position, the endoscope is pulled out of the catheter 11 through the tool hole 16*a*. Then, the medical tool is inserted through the tool hole 16*a*, and a work such as the collection of various specimens from the inside of the object or the treatment of the inside of the object is performed.

As described below, the catheter unit 100 is detachably attached with respect to the base unit 200. After the bendable medical device 1 is used, the user detaches the catheter unit 100 from the base unit 200, attaches a new catheter unit 100 to the base unit 200, and thus it becomes possible to use the bendable medical device 1 again.

The bendable medical device 1 includes an operation portion 400. In the present embodiment, the operation portion 400 is provided in the catheter unit 100. The operation portion 400 is operated by the user at the time of securing the catheter unit 100 with respect to the base unit 200 or detaching the catheter unit 100 from the base unit 200.

By connecting the endoscope, which is inserted in the catheter 11, to the monitor 4, an image captured by the endoscope can be displayed on the monitor 4. In addition, by connecting the monitor 4 to the control portion 3, a state of the bendable medical device 1 and information related to the control of the bendable medical device 1 can be displayed on the monitor 4. For example, the position of the catheter 11 in the inside of the object and information related to the navigation of the catheter 11 in the inside of the object can be displayed on the monitor 4. The monitor 4, the control portion 3, and the endoscope may be connected to each other in a wired manner or in a wireless manner. In addition, the monitor 4 and the control portion 3 may be connected to each other via the insertion unit 2.

Insertion Method of Bendable Medical Device

As described above, the user inserts the catheter 11 to the inside of the patient serving as the object. Specifically, through the insertion into the bronchial tube via the mouth or nose of the patient, it is possible to perform a work such as observing, collecting, and cutting the lung tissue. Two methods are provided for inserting the catheter 11 to the inside of the patient. One method is a method in which the user detaches the bendable medical device 1 from the insertion unit 2, and maneuvers the bendable medical device 1 by holding the bendable medical device 1 by hands and then moving the hands as intended by the user. Hereinafter, this method will be referred to as manual insertion.

Another method is a method in which the slider 2*b* of the insertion unit 2 linearly moves the moving stage 2*a* to which the bendable medical device 1 is attached. Movement via the slider 2*b* is driven by a motor, not shown, connected to the control portion 3, based on user instructions. Hereinafter, this method will be referred to as robot insertion.

By switching between two insertion methods of the manual insertion and the robot insertion, the flexible adaptation of the insertion of the catheter 11 to a necessary situation becomes possible. For example, when initially inserting the catheter 11 through a larger/wider anatomical structure of the patient, the manual insertion can facilitate the rapid advancement of the catheter 11, and, as a result, it is possible to save time. When the catheter 11 reaches more intricately twisted portion of the anatomical structure of the patient, the catheter 11 is switched to the robot insertion. Thereby, it is possible to insert the catheter 11 to a further smaller/narrower portion. In addition, the robot insertion is performed at a slower and more gradual speed to minimize abrasion and discomfort for the patient.

An imaginary line that passes through a center of the catheter 11 at the near end of the catheter 11 and extends along the extending direction (longitudinal direction) of the catheter 11 will be referred to as a reference axis A1 of the bendable medical device 1. When the catheter 11 becomes linear, the reference axis A1 is parallel to the extending direction of the catheter 11.

During the robot insertion, when the bendable medical device 1 (base unit 200) moves to one side in a direction along the reference axis A1 in conjunction with the moving stage 2*a*, the far end of the catheter 11 moves (advances) to enter the inside of the object. On the other hand, when the bendable medical device 1 (base unit 200) moves to the other side in the direction along the reference axis A1 in conjunction with the moving stage 2*a*, the far end of the catheter 11 moves (retracts) so as to be pulled out from the inside of the object. The movement of the moving stage 2*a* is achieved by the control portion 3 controlling an operation of the motor 2*c*.

In FIG. 2, an arrow D1 represents a moving direction (advancement direction) of the moving stage 2*a* when the bendable medical device 1 is advanced. An arrow D2 represents a moving direction (retraction direction) of the moving stage 2*a* when the bendable medical device 1 is retracted.

The advancement direction (arrow D1) and the retraction direction (arrow D2) of the moving stage 2*a* are directions substantially parallel to the reference axis A1 of the bendable medical device 1. However, if a configuration allows the catheter 11 to perform the insertion and extraction by the robot insertion, it is acceptable to configure such that the moving stage 2*a* moves in a direction intersecting with the reference axis A1. The moving stage 2*a* moves in the advancement direction (arrow D1) and the retraction direction (arrow D2) by the slider 2*b*. The slider 2*b* includes a rail (guide portion) extending in an elongated manner in the advancement direction (arrow D1) and the retraction direction (arrow D2), and a transmission mechanism that moves the moving stage 2*a* along the rail by a driving force of the motor 2*c* interconnected to the moving stage 2*a*.

Tilt Angle of Bendable Medical Device

As illustrated in FIG. 1, the insertion unit 2 is pivotably supported by the arm 6. The user can tilt the insertion unit

2 by holding a holding portion 2*h* of the insertion unit 2. A tilt angle of the bendable medical device 1 attached to the moving stage 2*a* of the insertion unit 2 is defined as an angle of the reference axis A1 of the bendable medical device 1 with respect to the horizontal (an imaginary horizontal plane perpendicular to the vertical direction).

The insertion unit 2 can tilt (pivotable, changeable in posture) around an axis perpendicular to the reference axis A1 between a posture in which the tilt angle of the bendable medical device 1 is minimized and a posture in which the tilt angle is maximized. In addition, in the present embodiment, a direction of a pivot axis of the insertion unit 2 when changing the tilt angle of the bendable medical device 1 is the horizontal direction (Y direction, described below) substantially perpendicular to the moving directions (arrows D1 and D2) of the moving stage 2*a*. A pivot range of the insertion unit 2 is restricted by a stopper, not shown, disposed in the arm 6.

Figure 3:
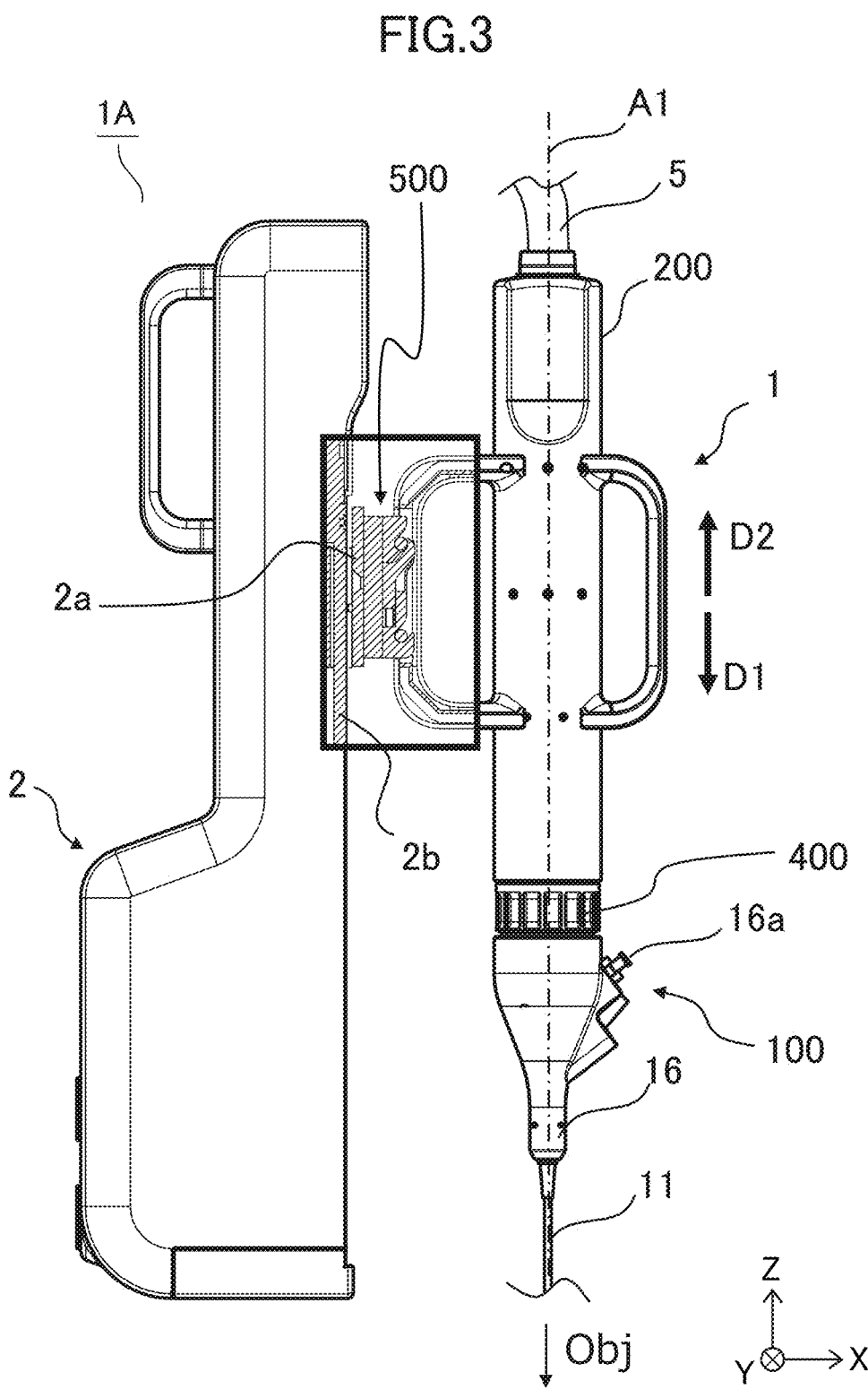
FIG. 3 is a side view illustrating the bendable medical device and the insertion unit.

The insertion unit 2 of the present embodiment can tilt such that the tilt angle of the bendable medical device 1 ranges from a minimum of 0 degree to a maximum of 90 degrees (FIG. 3). To be noted, the pivot range of the insertion unit 2 is not limited to this, and, for example, a maximum value of the tilt angle of the bendable medical device 1 may be less than 90 degrees.

As described above, the moving directions (arrows D1 and D2) of the moving stage 2*a* in the insertion unit 2 are directions substantially parallel to the reference axis A1 of the bendable medical device 1 attached to the moving stage 2*a*. That is, the insertion unit 2 is configured to be tiltable (pivotable, changeable in posture) such that the tilt angle of the moving direction of the moving stage 2*a* with respect to the horizontal changes.

In the state in which the tilt angle of the bendable medical device is maximized, the advancement direction (arrow D1) of the moving stage 2*a* becomes a direction that is directed downward in the vertical direction. In the present embodiment, in the state in which the tilt angle of the bendable medical device 1 is maximized, the advancement direction (arrow D1) and the retraction direction (arrow D2) of the moving stage 2*a* become substantially the vertical direction.

Attachment Configuration of Bendable Medical Device

As described above, the bendable medical device 1 of the present embodiment is configured to be switchable between the two insertion methods of the manual insertion and the robot insertion. Therefore, it is preferred to reduce a possibility of the bendable medical device 1 being inadvertently dropped. For example, at the time of attaching the bendable medical device 1 to the insertion unit 2, at the time of detaching the bendable medical device 1 from the insertion unit 2, and the like, it is preferred to reduce the possibility of the bendable medical device 1 being dropped against an intention of the user. In addition, it is desirable that operability for attaching and detaching the bendable medical device 1 with respect to the insertion unit 2 is high.

Figure 4:
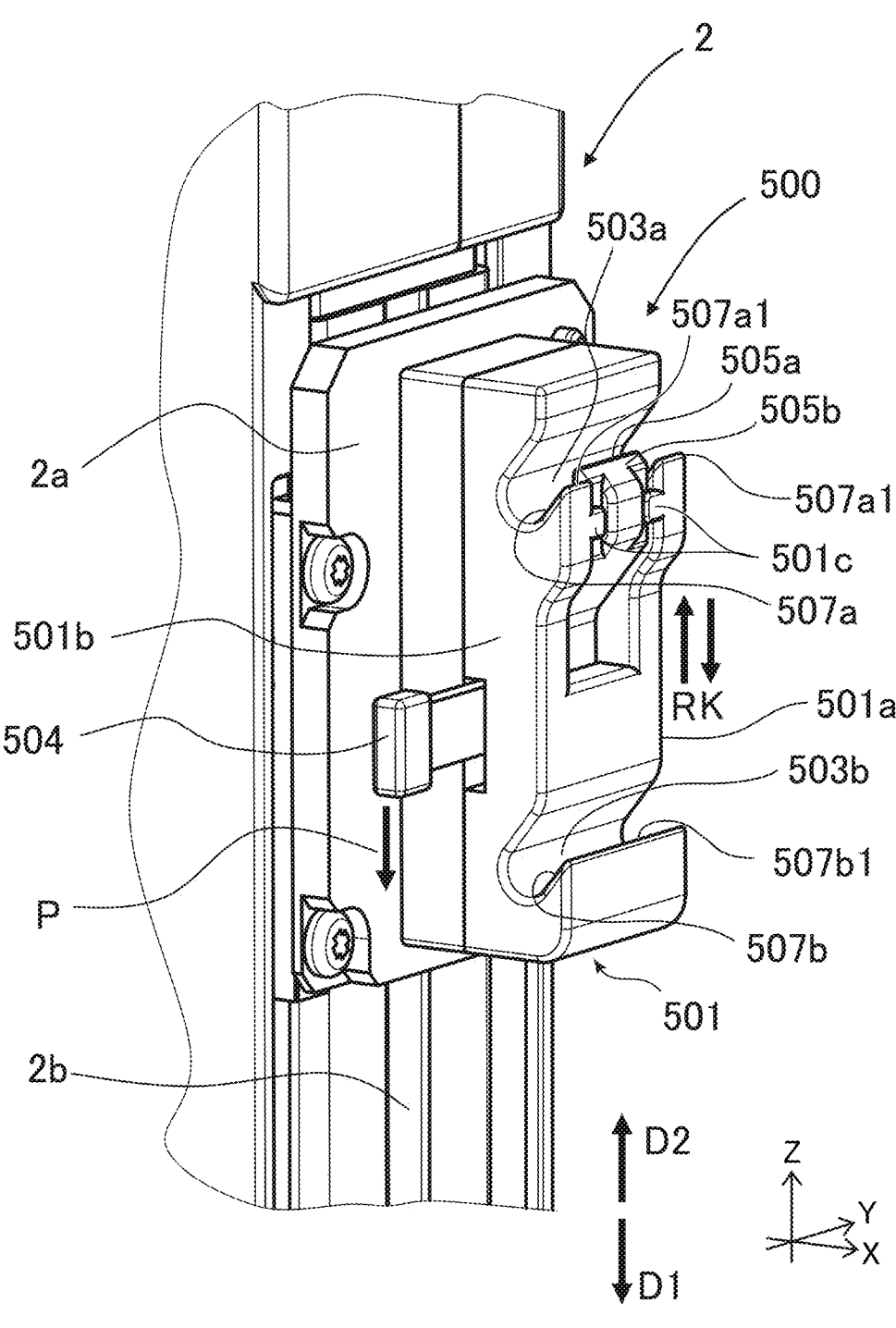
FIG. 4 is a perspective view illustrating an attachment portion of the insertion unit.
Figure 5:
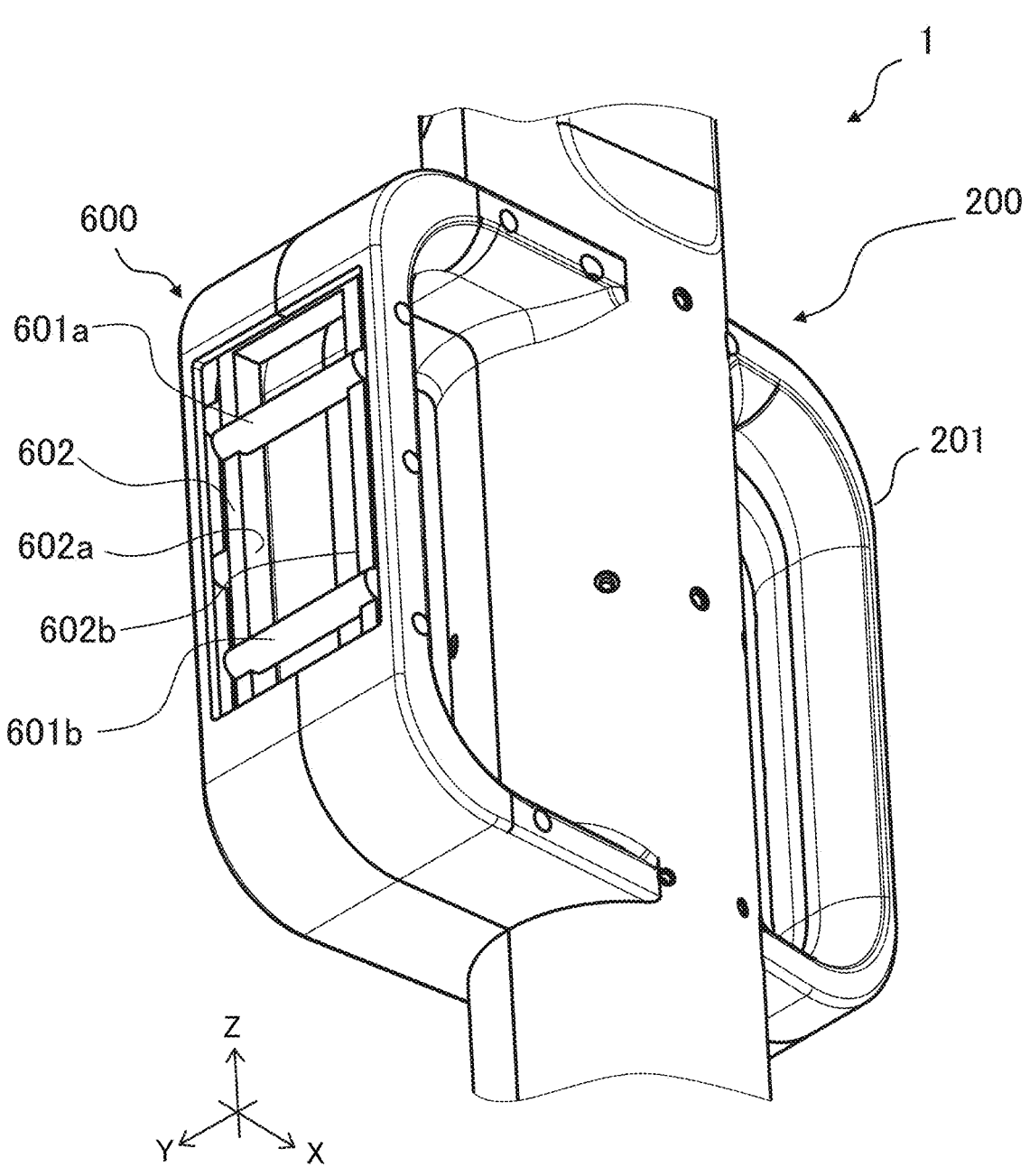
FIG. 5 is a perspective view illustrating an attached portion of the bendable medical device.

Using FIGS. 3 to 6C, connecting portions (500, 600) between the bendable medical device 1 and the insertion unit 2 will be described. FIG. 3 is a side view illustrating the bendable medical device 1 and the insertion unit 2, and illustrates a partial cross-sectional view of an area around the attachment portion 500 of the insertion unit 2. FIG. 4 is a perspective view illustrating the attachment portion 500 of the present embodiment with the bendable medical device 1 detached. FIG. 5 is a perspective view illustrating a portion 600 to be attached, which is a portion of the bendable medical device 1 to be attached to the attachment portion 500, in a state detached from the attachment portion 500.

Figure 6A:
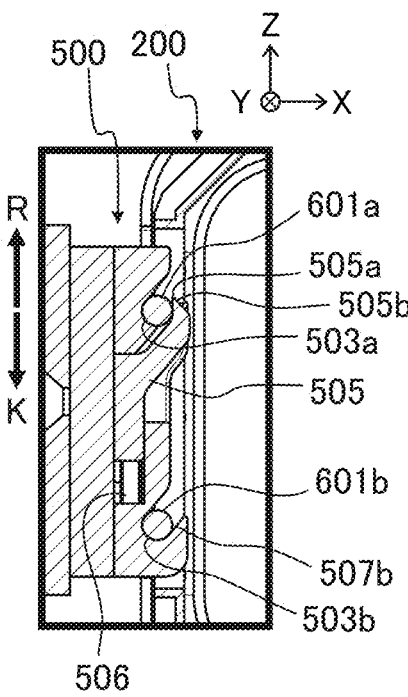
FIG. 6A is a diagram for describing an operation of the attachment portion.
Figure 6B:
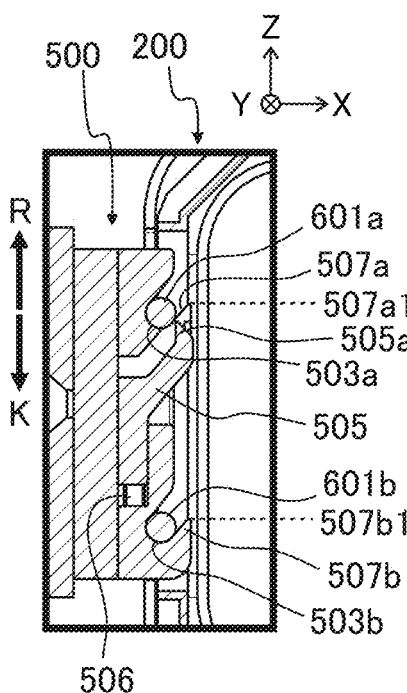
FIG. 6B is a diagram for describing the operation of the attachment portion.
Figure 6C:
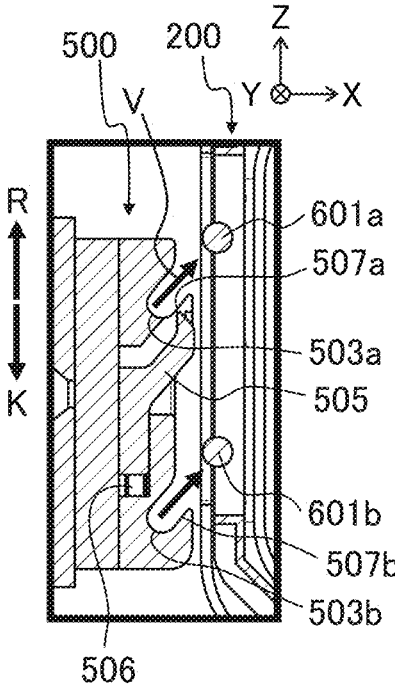
FIG. 6C is a diagram for describing the operation of the attachment portion.

FIGS. 6A to 6C are partial cross-sectional views for describing operations of the attachment portion 500 and the portion 600 to be attached. FIG. 6A illustrates a state in which the bendable medical device 1 is attached to the insertion unit 2 and the attachment portion 500 is in a locked state. FIG. 6B illustrates a state in which the bendable medical device 1 is attached to the insertion unit 2 and the attachment portion 500 is in an unlocked state. FIG. 6C illustrates an intermediate state of the bendable medical device 1 that is being detached from the insertion unit 2.

FIGS. 3 to 6C illustrate the medical apparatus 1A in a state in which the tilt angle of the bendable medical device 1 is maximized. In the following descriptions, unless specifically stated, shapes, positional relationships, and the like of components constituting the attachment portion 500 and the portion 600 to be attached will be described based on the state in which the tilt angle of the bendable medical device 1 is maximized. In addition, in a case where the medical apparatus 1A is installed on the horizontal surface, an upward vertical direction will be referred to as a Z direction, and directions that are perpendicular to the Z direction and perpendicular to each other will be referred to as an X direction and a Y direction. Further, for the X, Y, and Z directions, the directions indicated by arrows will be referred to as a positive (+) direction, directions opposite to the arrows will be referred to as a negative (–) direction, and will be represented by adding symbols of "+" or "–" as necessary.

As illustrated in FIG. 3, the bendable medical device 1 is detachably attached (connected) with respect to the attachment portion 500 of the insertion unit 2. The attachment portion 500 is disposed on the moving stage 2a. When the moving stage 2a is linearly moved by the slider 2b, the attachment portion 500 is linearly moved in the D1 and D2 directions integrally with the moving stage 2a.

As illustrated in FIG. 4, the attachment portion 500 of the insertion unit 2 (moving stage 2a) includes two recess portions 503a and 503b, restriction surfaces 507a and 507b, a locking member 505, a release lever 504, and a frame 501.

The recess portion 503a (first recess portion) of the moving stage 2a is in a recessed shape that can accommodate a mounting shaft 601a (FIG. 5), described below, of the bendable medical device 1. In a case when viewed in the Y direction, the recess portion 503a of the present embodiment is in a groove shape that is recessed downward (–Z direction side) toward the –X direction side. In addition, the recess portion 503a opens toward the +X direction side and upward (+Z direction side).

The recess portion 503b (second recess portion) of the moving stage 2a is in a recessed shape that can accommodate a mounting shaft 601b (FIG. 5) of the bendable medical device 1. In the case when viewed in the Y direction, the recess portion 503b of the present embodiment is in a groove shape that is recessed downward (–Z direction side) toward the –X direction side. In addition, the recess portion 503b opens toward the +X direction side and upward (+Z direction side).

The recess portions 503a and 503b hold held portions (mounting shafts 601a and 601b) of the bendable medical device 1 such that the moving stage and the bendable medical device 1 transition to an integrally moving state. In addition, the recess portions 503a and 503b are also portions that support the weight of the bendable medical device 1.

In the present embodiment, the two recess portions 503a and 503b are shaped in grooves that, in the case when viewed in the Y direction, extend substantially parallel to each other. The recess portions 503a and 503b are disposed in the frame 501 of the moving stage 2a. In the present embodiment, an attachment direction (installation direction) of the bendable medical device 1 (portion 600 to be attached) with respect to the insertion unit 2 (attachment portion 500) is a direction in which the mounting shafts 601a and 601b are oriented toward bottom portions of the recess portions 503a and 503b along the groove shape. In addition, a detachment direction of the bendable medical device 1 (portion 600 to be attached) from the insertion unit 2 (attachment portion 500) is a direction in which the mounting shafts 601a and 601b are oriented from the bottom portions to openings of the recess portions 503a and 503b along the groove shape.

As illustrated in FIG. 5, the portion 600 to be attached of the bendable medical device 1 includes two mounting shafts 601a and 601b, and a frame 602. The mounting shafts 601a and 601b are supported by the frame 602. The mounting shafts 601a and 601b of the present embodiment are in a cylindrical shape that extends in an elongated manner in the Y direction. The frame 602 is secured with respect to a frame of the base unit 200 of the bendable medical device 1.

The mounting shaft 601a is an example of a held portion (locked portion, first held portion) that is received in the recess portion 503a of the moving stage 2a in a case where the bendable medical device 1 is attached to the moving stage 2a. The mounting shaft 601b is an example of a held portion (locked portion, second held portion) that is received in the recess portion 503b of the moving stage 2a in the case where the bendable medical device 1 is attached to the moving stage 2a.

As illustrated in FIG. 4, the locking member 505 of the moving stage 2a is movable to a position (locking position, projecting position, FIG. 6A) projecting into an internal space of the recess portion 503a, and to a position (release position, retracted position, FIGS. 6B and 6C) retracted from the internal space of the recess portion 503a. The locking member 505 is supported by the frame 501 of the moving stage 2a in a manner linearly movable between the locking position and the release position (arrows R and K). The locking position is a position at which the locking member 505 locks (restricts disengagement) the mounting shaft 601a within of the recess portion 503a, and the release position is a position at which the locking member 505 allows the mounting shaft 601a to disengage from the recess portion 503a.

The locking member 505 is urged toward a direction (arrow R) from the release position toward the locking position by a compression spring 506 (refer to FIG. 6A), serving as an urging member. The compression spring 506 of the present embodiment is a torsion coil spring arranged between the locking member 505 and the frame 501 of the moving stage 2a.

The locking member 505 includes a locking hook 505a for locking the mounting shaft 601a. In a case where the locking member 505 is positioned at the locking position, the locking hook 505a projects into the recess portion 503a, and, in a case where the locking member 505 is positioned at the release position, the locking hook 505a retracts from the recess portion 503a. In the case where the locking member 505 is positioned at the locking position, the locking hook 505a engages with the mounting shaft 601a at a position different from a wall surface of the recess portion 503a, and holds (grips) the mounting shaft 601a together with a wall surface of the recess portion 503a.

In addition, the frame 501 of the moving stage 2a includes a projecting portion 501c holding a surface of the lock member 505 that is opposite from a surface of the lock member 505 where the locking hook 505a faces the recess portion 503a. The projecting portion 501c can restrict the bending or a posture change of the locking member 505 so as to ensure that the locking hook 505a does not move in a case where the locking hook 505a of the locking member 505 receives a force from the mounting shaft 601a.

The release lever 504 of the moving stage 2a is an example of an operation portion that is operated by the user to move the locking member 505 from the locking position to the release position. The user can move the locking member 505 from the locking position to the release position by pressing the release lever 504 in an arrow P direction while resisting the urging force of the compression spring 506. The release lever 504 of the present embodiment is formed integrally with the locking member 505.

Instead of a configuration where the locking member 505 and the release lever 504 are formed integrally, it is acceptable to configure such that a locking member 505, which is a separate member from the operation portion, moves from the locking position to the release position in conjunction with an operation of the operation portion. In addition, instead of the operation portion, for example, it is acceptable to configure such that an actuator disposed in the insertion unit 2 moves the locking member 505 from the locking position to the release position based on instructions input by the user via the input apparatus 3b.

The restriction surface 507a (first restriction surface) of the moving stage 2a is a surface that faces the recess portion 503a. The restriction surface 507a is disposed in the frame 501 of the moving stage 2a. An end portion 507a1 of the restriction surface 507a in a direction from the bottom portion toward the opening of the recess portion 503a configures part of an opening edge of the recess portion 503a. In the state in which the tilt angle of the bendable medical device 1 is maximized (for example, refer to FIGS. 3 and 4), the end portion 507a1 that is an upper end of the restriction surface 507a forms a lower edge of the opening of the recess portion 503a.

The restriction surface 507b (second restriction surface) of the moving stage 2a is a surface that faces the recess portion 503b. The restriction surface 507b is disposed in the frame 501 of the moving stage 2a. An end portion 507b1 of the restriction surface 507b in a direction from the bottom portion toward the opening of the recess portion 503b configures part of an opening edge of the recess portion 503b. In the state in which the tilt angle of the bendable medical device 1 is maximized (for example, refer to FIGS. 3 and 4), the end portion 507b1 that is an upper end of the restriction surface 507b forms a lower edge of the opening of the recess portion 503b.

With the configuration described above, as described below, the restriction surface 507a and 507b reduce the possibility of the bendable medical device 1 being inadvertently dropped in an unlocked state (FIG. 6B) of the attachment portion 500.

In the state in which the tilt angle of the bendable medical device is maximized, the restriction surfaces 507a and 507b of the present embodiment are an inclined surface that is inclined upward with respect to the horizontal as it approaches the openings of the recess portions 503a and 503b. Inclination angles of the restriction surfaces 507a and 507b are arbitrary, but are set to be capable of restricting the dropping of the bendable medical device 1 and by taking into consideration aspects such as the operability for attaching and detaching the bendable medical device 1 with respect to the moving stage 2a.

As illustrated in FIG. 4, the frame 501 of the moving stage 2a includes a first side surface 501a on the +Y direction side and a second side surface 501b on the −Y direction side. On the other hand, as illustrated in FIG. 5, the frame 602 of the bendable medical device 1 includes a first side surface 602a on the +Y direction side and a second side surface 602b on the −Y direction side In a case where the bendable medical device 1 is attached to the moving stage 2a, the first side surface 501a of the moving stage 2a faces the first side surface 602a of the bendable medical device 1 in the Y direction, and the second side surface 501b of the moving stage 2a faces the second side surface 602b of the bendable medical device 1 in the Y direction. Thereby, regarding the Y direction, the bendable medical device 1 is positioned with respect to the moving stage 2a.

That is, the first and second side surfaces 501a and 501b of the moving stage 2a restrict a positional shift of the bendable medical device 1 with respect to the moving stage 2a regarding the Y direction, which is an axial direction of the mounting shafts 601a and 601b. A configuration that restricts the positional shift of the bendable medical device 1 in the Y direction is not limited to this, and, for example, by disposing an elongated rib (projection) extending in the Z direction on the frame 501 of the moving stage 2a or the frame 602 of the bendable medical device 1, it is acceptable to dispose a groove, which fits into this rib, in the other frame.

Hereinafter, with reference to FIGS. 6A to 6C, an operation of the attachment portion 500 will be described.

As illustrated in FIG. 6A, when the locking member 505 is positioned at the locking position, the attachment portion 500 transitions to a locked state in which the mounting shaft 601a of the bendable medical device 1 locks by the locking hook 505a at the distal end of the locking member 505.

In the locked state, when viewed from an opening side (right upper side in the figure) of the recess portion 503a, the locking hook 505a of the locking member 505 overlaps at least part of the mounting shaft 601a that is positioned inside of the recess portion 503a. That is, in the locked state, the locking member 505 is positioned at a position that interferes with a moving direction (arrow V in FIG. 6C) of the mounting shaft 601a at the time of detaching the bendable medical device 1 from the moving stage 2a. Therefore, the disengagement of the mounting shaft 601a from the recess portion 503a is restricted, and the detachment of the bendable medical device 1 from the moving stage 2a is restricted.

To be noted, in the state in which the tilt angle of the bendable medical device 1 is maximized, a gravitational force acting on the locking member 505 aligns in a direction along a direction (arrow K) from the locking position toward the release position. However, the locking member 505 is held at the locking position by the urging force of the compression spring 506 in the arrow R direction while resisting the gravitational force.

In the present embodiment, while the locking member 505 directly locks only one of the mounting shaft 601a, since the other mounting shaft 601b fits into the recess portion 503b, a pivot of the bendable medical device 1 around the mounting shaft 601a as a center is also restricted. That is, the recess portion 503b is in a groove shape extending in a direction intersecting with a tangential direction (left-right direction in FIG. 6A) of an arc centered around an axis of the mounting shaft 601a that is fitted into the recess portion 503a. Therefore, even if, in the state in which the mounting shaft 601a is locked into the recess portion 503a, the bendable medical device 1 is attempted to be pivoted around the mounting shaft 601*a* as a center, the mounting shaft 601*b* interferes with a wall surface of the recess portion 503*b*, and the bendable medical device 1 does not pivot.

To be noted, separately from the locking member 505, it is acceptable to additionally arrange a locking member that locks the mounting shaft 601*b* within of the recess portion 503*b*.

As illustrated in FIG. 6B, when the user operates the release lever 504 (FIG. 4) in a predetermined operation direction (arrow P), the locking member 505 is moved from the locking position to the release position (arrow K). Thereby, the attachment portion 500 transitions to the unlocked state in which the lock of the mounting shaft 601*a* of the bendable medical device 1 is released.

In the unlocked state, the locking hook 505*a*, which has overlapped the mounting shaft 601*a* in the locked state, of the locking member 505 retracts to a position that does not overlap the mounting shaft 601*a*. That is, in the release of the locked state, the locking member 505 is positioned at a position that does not interfere with the moving direction (arrow V in FIG. 6C) of the mounting shaft 601*a* at the time of detaching the bendable medical device 1 from the moving stage 2*a*. To be noted, since the locking member 505 is continuously receiving the urging force of the compression spring 506, when the user releases the hand from the release lever 504, the locking member 505 again moves from the release position to the locking position, and the attachment portion 500 returns to the locked state of FIG. 6A.

As illustrated in FIG. 6C, when the attachment portion 500 is in the unlocked state, the user holds the bendable medical device 1 and moves it in an arrow V direction, the mounting shafts 601*a* and 601*b* are disengaged from the recess portions 503*a* and 503*b* of the moving stage 2*a*. Thereby, it is possible to detach the bendable medical device 1 from the moving stage 2*a*.

In the case of attaching the bendable medical device 1 to the moving stage 2*a*, the procedure at the time of the detachment described above may be reversed. That is, while transitioning the attachment portion 500 to the unlocked state by pressing the release lever 504 of the attachment portion 500, the user moves the bendable medical device 1 in the attachment direction opposite to the arrow V direction, and fits the mounting shafts 601*a* and 601*b* into the recess portions 503*a* and 503*b* of the moving stage 2*a*. Thereafter, when the hand is released from the release lever 504, the locking member 505 moves from the release position to the locking position by the urging force of the compression spring 506, the attachment portion 500 transitions to the locked state. Thereby, the bendable medical device 1 is attached to the moving stage 2*a*, and transitions to a state of moving integrally with the moving stage 2*a*.

To be noted, it is possible to configure such that, by disposing a contacted surface 505*b* (FIG. 4) that is made to come into contact with the mounting shaft 601*a* of the bendable medical device 1, the locking member 505 is automatically moved from the locking position to the release position at the time of attaching the bendable medical device 1. In this case, the user may move the bendable medical device 1 in the attachment direction opposite to the arrow V direction without operating the release lever 504. In a course where the mounting shaft 601*a* moves toward the recess portion 503*a*, the mounting shaft 601*a* comes into contact with the contacted surface 505*b* of the locking member 505 positioned at the locking position. Then, the locking member 505 receives a force from the mounting shaft 601*a* in a direction (arrow K) toward the release position, and retracts in a manner being pushed aside by the mounting shaft 601*a*. When the mounting shaft 601*a* passes by the locking hook 505*a* of the locking member 505, by the urging force of the compression spring 506, the locking member 505 moves to the locking position, and the attachment portion 500 transitions to the locked state.

Act of Restriction Surface

Figure 7A:
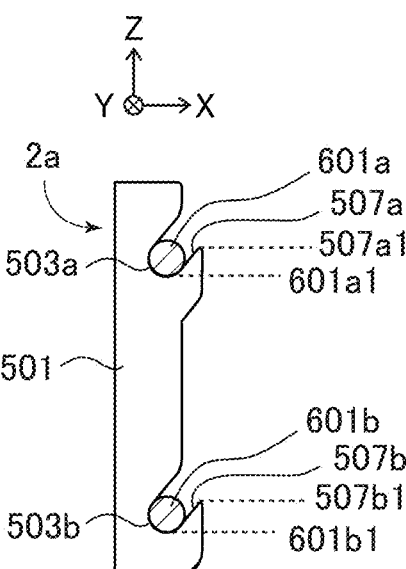
FIG. 7A is a schematic diagram illustrating the attachment portion according to the embodiment.

Acts of the restriction surfaces 507*a* and 507*b* disposed in the moving stage 2*a* will be described. FIG. 7A is a schematic diagram illustrating a state that corresponds to FIG. 6B of the attachment portion 500 of the present embodiment.

As illustrated in FIGS. 6B and 7A, in a state in which the mounting shaft 601*a* is positioned inside of the recess portion 503*a* and the tilt angle of the bendable medical device 1 is maximized, the end portion 507*a*1 that is the upper end of the restriction surface 507*a* is positioned above the lower end 601*a*1 of the mounting shaft 601*a*. That is, in the present embodiment, in the state in which the held portion is positioned inside of the recess portion and the tilt angle of the bendable medical device is maximized, the restriction surface extends upward such that the upper end of the restriction surface is positioned above the lower end of the held portion. In addition, in the state in which the held portion is positioned inside of the recess portion and the tilt angle of the bendable medical device is maximized, the upper end (end portion 507*a*1) of the restriction surface forms the lower edge of the opening of the recess portion. That is, the restriction surface is a surface that faces the recess portion and is a different surface from which is continuous with the upper end of the opening of the recess portion (in FIG. 6B, wall surface on an upper left side of the recess portion 503*a*).

With this configuration, it becomes possible to reduce the possibility of the bendable medical device 1 being inadvertently dropped.

As a comparative example, a configuration in which the recess portion 503*a* extends horizontally to the opening in the state in which the tilt angle of the bendable medical device 1 is maximized is considered. In this case, it is assumed that, in the state in which the tilt angle of the bendable medical device 1 is maximized, in a case where the locking member 505 is moved to the release position, the bendable medical device 1 receives a force in the X direction (horizontal component of a direction toward the opening of the recess portion 503*a*). In this case, there is a possibility that the mounting shaft 601*a* reaches the opening of the recess portion 503*a* without being obstructed by obstacles and is disengaged from the recess portion 503*a*.

On the other hand, it is assumed that, in the present embodiment, in the state in which the tilt angle of the bendable medical device 1 is maximized, in the case where the locking member 505 is moved to the release position, the bendable medical device 1 receives the force in the X direction (horizontal component of the direction toward the opening of the recess portion 503*a*). Since, in this case, the movement of the mounting shaft 601*a* is restricted by the restriction surface 507*a*, the possibility of the mounting shaft 601*a* being disengaged from the recess portion 503*a* and the bendable medical device 1 being inadvertently dropped is reduced. Here, while FIG. 6B represents a state in a middle of a detachment operation of the bendable medical device 1 as one scene where an act of drop prevention by the restriction surface 507*a* is activated, also, during an attachment operation of the bendable medical device 1, the presence of the restriction surface 507*a* reduces the possibility of the bendable medical device 1 being dropped.

In addition, in the present embodiment, the plurality of restriction surfaces 507a and 507b (first restriction surface, second restriction surface) are arranged corresponding to each of the plurality of mounting shafts 601a and 601b (first held portion, second held portion). In the state in which the mounting shaft 601b is positioned inside of the recess portion 503b and the tilt angle of the bendable medica device 1 is at its maximum, the end portion 507b1 that is the upper end of the restriction surface 507b is positioned above the lower end 601b1 of the mounting shaft 601b, and forms the lower edge of the opening of the recess portion 503b. Therefore, it is possible to further reduce the possibility of the bendable medical device 1 being inadvertently dropped.

To be noted, even in the state in which the tilt angle of the bendable medical device 1 is at its maximum, the user can detach the bendable medical device 1 from the insertion unit 2 without obstruction. In this case, after moving the locking member 505 to the release position, the user may move the bendable medical device 1 in a predetermined detachment direction (arrow V in FIG. 6C) that includes an upward component in the vertical direction.

Variant Examples

In the embodiment described above, as the restriction surfaces 507a and 507b, an inclined surface inclined with respect to the horizontal in a manner extending upward as it approaches the openings of the recess portions 503a and 503b in the state in which the tilt angle of the bendable medical device 1 is at its maximum is illustrated as an example. The restriction surface is not limited to this, and, for example, may be those illustrated in FIGS. 7B and 7C.

Figure 7B:
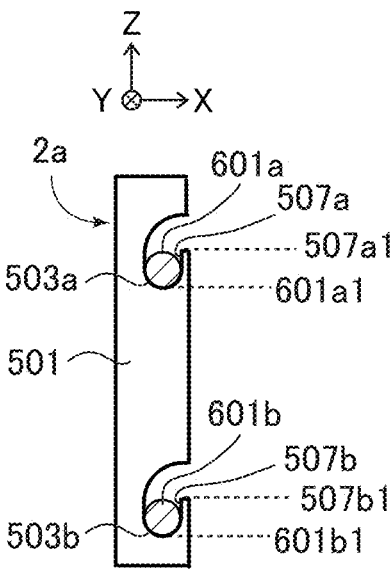
FIG. 7B is a schematic diagram illustrating a variant example of the attachment portion.

In a variant example illustrated in FIG. 7B, the recess portions 503a and 503b are curved (bent) between the openings and the bottom portions. In the state in which the tilt angle of the bendable medical device 1 is at its maximum, the recess portions 503a and 503b extend upward from the bottom portions in the vertical direction (+Z direction), and open toward one side (+X direction) of the horizontal direction.

The restriction surfaces 507a and 507b are surfaces that face the recess portions 503a and 503b and, in the state in which the tilt angle of the bendable medical device 1 is at its maximum, extend substantially in the vertical direction. In the state in which the mounting shafts 601a and 601b are positioned inside of the recess portions 503a and 503b and the tilt angle of the bendable medical device 1 is at its maximum, the end portions 507a1 and 507b1 on the upper sides of the restriction surfaces 507a and 507b are positioned above the lower ends 601a1 and 601b1 of the mounting shafts. In addition, the end portions 507a and 507b1 on the upper sides of the restriction surfaces 507a and 507b form the lower edges of the openings of the recess portions 503a and 503b. Therefore, the restriction surfaces 507a and 507b can restrict the bendable medical device 1 being dropped.

Figure 7C:
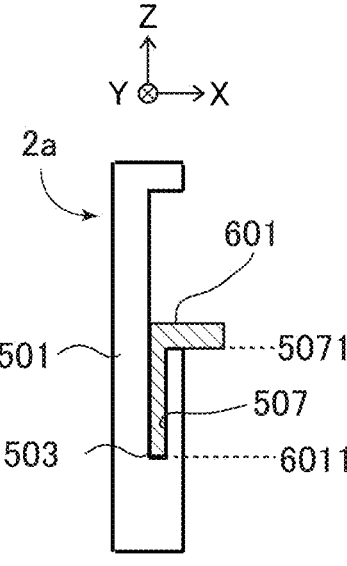
FIG. 7C is a schematic diagram illustrating a variant example of the attachment portion.

Also in a variant example illustrated in FIG. 7C, a recess portion 503 bends between an opening portion and a bottom portion. In the state in which the tilt angle of the bendable medical device 1 is at its maximum, the recess portion 503 extends from the bottom portion upward (+Z direction) in the vertical direction and opens toward one side (+X direction) of the horizontal direction. The bendable medical device 1 includes an L shaped attachment member 601. At the time of attaching the bendable medical device 1, after having been inserted with respect to the opening of the recess portion 503 toward the –X direction, by being moved toward the bottom portion of the recess portion 503 in the –Z direction, the attachment member 601 is positioned inside of the recess portion 503.

The restriction surface 507 is a surface that faces the recess portion 503 and, in the state in which the tilt angle of the bendable medical device 1 is at its maximum, extends substantially in the vertical direction. In a state in which the attachment member 601 is positioned inside of the recess portion 503 and the tilt angle of the bendable medical device 1 is at its maximum, an end portion 5071 on the upper side of the restriction surface 507 is positioned above a lower end 6011 of the attachment member. In addition, the end portion 5071 on the upper side of the restriction surface 507 forms a lower edge of the opening of the recess portion 503. Therefore, the restriction surface 507 can restrict the bendable medical device 1 being dropped.

Incidentally, in the example of FIG. 7A, as the restriction surfaces 507a and 507b, inclined surfaces aligned in a linear direction from the bottom portions to the openings of the recess portions 503a and 503b are adopted. In other words, the recess portions 503a and 503b have a groove shape recessed in an inclination direction of the restriction surfaces 507a and 507b. In the variant examples of FIGS. 7B and 7C, at the time of attaching and detaching the bendable medical device 1, the user moves the bendable medical device 1 such that the mounting shafts 601a and 601b or 601 move along a bend (curve) of the recess portions 503a and 503b or 503. In comparison with this, in the example of FIG. 7A, at the time of attaching and detaching the bendable medical device 1, the user may move the bendable medical device 1 such that the mounting shafts 601b and 601b move linearly along the restriction surfaces 507a and 507b, and it is possible to attain more favorable operability.

The variant examples of FIGS. 7B and 7C are examples of configurations in which shapes of the recess portion and the restriction surface are different from the example of FIG. 7A. The variant example of FIG. 7C is an example of a configuration in which the bendable medical device 1 includes a single held portion and the insertion unit 2 includes a single recess portion and a single restriction surface. Shapes, quantities, and arrangements, and the likes of the held portions, recess portions, restriction surfaces, and other constituting elements are not limited to those that are exemplified, and can be appropriately modified.

In addition, in the examples described above, the configuration in which the locking member 505 locks the held portion within the recess portion by directly engaging with the held portion (mounting shaft 601a) is exemplified. It is not limited to this, and it is acceptable that the locking member 505 locks the held portion within the recess portion by engaging with portions other than the held portion of the bendable medical device 1. For example, the frame 602 of the bendable medical device 1 may have a recessed shape that serves as an engaged portion with which the locking member 505 engages at a position different from the mounting shaft 601a. In this case, when the locking member 505 fits into this recessed shape, the movement of the bendable medical device 1 in a direction in which the mounting shaft 601a moves from the bottom portion to the opening of the recess portion 503a is restricted.

As described above, the present invention can reduce a possibility of the bendable medical device being dropped.

Other Embodiments

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A medical apparatus comprising:

a bendable medical device including a bendable body and a held portion, the bendable body being bendable and configured to be inserted in an object; and an insertion unit including a moving body to which the bendable medical device is detachably attached, and a driving portion configured to move the moving body for advancing and retracting the bendable body with respect to the object, wherein the insertion unit is tiltable so as to change a tilt angle of the bendable medical device, which is attached to the moving body, with respect to a horizontal, wherein the moving body includes a recess portion configured to accommodate the held portion in a case where the bendable medical device is attached to the moving body, a locking member that is movable between a locking position for locking the held portion within the recess portion and a release position for allowing the held portion to be disengaged from the recess portion, and a restriction surface facing the recess portion, and wherein, in a state in which the held portion is positioned within the recess portion and the tilt angle is maximized, the restriction surface extends upward such that an upper end of the restriction surface is positioned above a lower end of the held portion, and the upper end of the restriction surface forms a lower edge of an opening of the recess portion.

2. The medical apparatus according to claim 1, wherein, in a state in which the tilt angle is maximized, the restriction surface is inclined with respect to the horizontal in a manner that the restriction surface extends upward as the restriction surface approaches the opening of the recess portion.

3. The medical apparatus according to claim 2, wherein the recess portion is in a groove shape that is recessed in an inclination direction of the restriction surface, and wherein, the held portion is configured to fit into and disengage from the recess portion in a case where the bendable medical device is moved in a direction along the inclination direction.

4. The medical apparatus according to claim 1, wherein the held portion, the recess portion, and the restriction surface are a first held portion, a first recess portion, and a first restriction surface, respectively, wherein the bendable medical device includes a second held portion, wherein the moving body includes a second recess portion configured to accommodate the second held portion in the case where the bendable medical device is attached to the moving body, and a second restriction surface facing the second recess portion, wherein, in a state in which the second held portion is positioned within the second recess portion and the tilt angle is maximized, the second restriction surface extends upward such that an upper end of the second restriction surface is positioned above a lower end of the second held portion, and the upper end of the second restriction surface forms a lower edge of an opening of the second recess portion.

5. The medical apparatus according to claim 1, wherein the locking member includes a locking hook for locking the held portion within the recess portion, and wherein the locking hook is configured to project into the recess portion in a case where the locking member is positioned at the locking position and to retract from the recess portion in a case where the locking member is positioned at the release position.

6. The medical apparatus according to claim 1, wherein, in the state in which the tilt angle is maximized, the moving body is configured to move downward for advancing the bendable body and to move upward for retracting the bendable body.

7. The medical apparatus according to claim 1, wherein the insertion unit includes a guide portion configured to guide a moving direction of the moving body, and wherein in the state in which the tilt angle is maximized, the moving direction is substantially a vertical direction.

8. The medical apparatus according to claim 1, wherein the insertion unit includes an operation portion configured to be operated for moving the locking member from the locking position to the release position.

9. The medical apparatus according to claim 1, wherein the driving portion is a first driving portion, wherein the bendable medical device includes a second driving portion configured to bend the bendable body, wherein the medical apparatus further comprises a control portion configured to control the second driving portion, and a cable electrically connecting the control portion and the bendable medical device, and wherein, in either state where the bendable medical device is attached to the insertion unit or the bendable medical device is detached from the insertion unit, the bendable medical device is configured to bend the bendable body by the second driving portion based on control of the control portion.

* * * * *